United States Patent [19]

Helmlinger et al.

[11] 4,375,428
[45] Mar. 1, 1983

[54] 2-SUBSTITUTED-1-ACETOXY AND HYDROXY-1-METHYL-CYCLOHEXANES

[75] Inventors: Daniel Helmlinger, Dübendorf; Peter Naegeli, Wettingen, both of Switzerland

[73] Assignee: Givaudan Corporation, Clifton, N.J.

[21] Appl. No.: 187,880

[22] Filed: Sep. 17, 1980

Related U.S. Application Data

[62] Division of Ser. No. 966,427, Dec. 4, 1978, Pat. No. 4,277,618.

[30] Foreign Application Priority Data

Dec. 12, 1977 [LU] Luxembourg .......................... 78670
Oct. 30, 1978 [CH] Switzerland ....................... 11175/78

[51] Int. Cl.³ ............................................. A61K 7/46
[52] U.S. Cl. ............................ 252/522 R; 252/174.11; 424/65; 424/70; 131/276
[58] Field of Search ................................. 252/522 R

[56] References Cited

FOREIGN PATENT DOCUMENTS

2819594 11/1979 Fed. Rep. of Germany ... 252/522 R
85403 12/1966 German Democratic Rep. .................................. 252/522 R

*Primary Examiner*—Thomas A. Waltz
*Attorney, Agent, or Firm*—Robert F. Tavares

[57] ABSTRACT

Novel odorants, having the formula

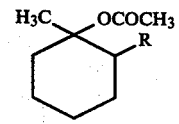

wherein R represents sec. butyl, tert. butyl or cyclohexyl.

A process for preparing the novel odorants from novel intermediates and fragrance compositions containing the odorants are also taught.

4 Claims, No Drawings

2-SUBSTITUTED-1-ACETOXY AND HYDROXY-1-METHYL-CYCLOHEXANES

This is a division of application Ser. No. 966,427, filed Dec. 4, 1978, now U.S. Pat. No. 4,277,618.

FIELD OF THE INVENTION

This invention relates to the field of fragrances.

SUMMARY OF THE INVENTION

See "Abstract of the Disclosure" above.

DESCRIPTION OF THE PREFERRED EMBODIMENTS

The invention is concerned with novel odorants, namely compounds of the general formula:

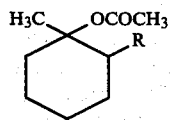
I wherein R represents sec.-butyl, tert.-butyl or cyclohexyl.

The invention is also concerned with a process for the manufacture of these novel compounds of formula I. This is characterised in that a compound of the general formula:

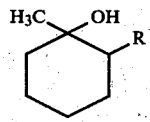
II wherein R has the above significance, is treated with an acetylating agent.

The esterification of the alcohols II is preferably carried out by using the acetyl halides. Advantageously, the reaction is carried out in the presence of tertiary amines, such as pyridine or dimethylaniline, or in the presence of alkali metal acetates or alkaline earth metal acetates, or in the presence of other organic bases. Pyridine and dimethylanilinne are preferred.

However, the reaction can also be carried out using the acid anhydride; thus, the acetates I are obtainable by reaction of II with acetic acid anhydride at temperatures between 0° and 30° C., with reaction times of 2-5 days, using catalytic amounts of phosphoric acid or of any other customary catalyst; the esterification can however also be carried out by using the acid anhydride at the reflux temperature (or, generally, between ca. 20° and 140°), if appropriate with addition of an alkali metal salt of acetic acid; the reaction time can be, e.g., 2–30 hours. The reaction time of course varies depending on the nature of the reactants employed. The reactions can in every case be carried out with the aid of solvents, such as aromatics, e.g. benzene or toluene, or aliphatics, e.g. hexane or heptane, or chlorinated aliphatics. Finally, a tertiary amine can also serve as the solvent.

The esters I are advantageously purified by distillation under reduced pressure; they are colourless to slightly yellowish-coloured liquids or low-melting crystalline substances, and are insoluble in water but soluble in organic solvents, such as, e.g., alcohols, ethers, ketones, esters, hydrocarbons and halogenated hydrocarbons.

The compounds of the general formula II which serve as starting materials for the process in accordance with the invention are novel and are also a subject of the present invention; they may be obtained by reacting a compound of the general formula

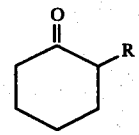
III wherein R has the above significance, with an organometallic compound of the general formula

MCH₃   IV wherein M represents an alkali metal or the group MgX, and wherein X is halogen.

The reaction of the ketone with the appropriate Grignard compound is preferred. In respect of the solvents, reaction temperature and amounts of reactants to be employed, the guidelines in the literature can be followed.

In the case of the Grignard compound, the reaction will thus be carried out, e.g., in solvents such as ethers, e.g. diethyl ether, tetrahydrofuran etc., or in hydrocarbons with addition of ethers, and at temperatures of (preferably) 0° C. to 50° C.

Normally, the Grignard compound and the ketone will be employed in the stoichiometric amounts, though, e.g., an excess of up to 20% of Grignard compound or ketone has no adverse effect on the course of the reaction.

In the case of the methyl-metal compounds, it is advantageous to employ the usual solution of methyl-lithium in diethyl ether at a temperature range of −75° C. to ca. 35° C., preferably at −35° C. to room temperature.

The alcohols II can be purified, e.g., by distillation under reduced pressure (approximately 0.1–5 mm Hg). They are colourless to pale yellowish-coloured liquids and are insoluble in water but soluble in alcohols, ketones, ethers, esters and hydrocarbons.

The esters I [as well as the alcohols II] of the present invention exist as cis-trans-stereoisomers, and the odour characteristics of these isomers are somewhat different. The isomers can be separated in accordance with the customary methods known for the separation of such stereoisomers. It has been found that fractional distillation of the corresponding alcohols under reduced pressure leads to separation of the isomers, and these can in turn again be reacted, in accordance with the methods described above, to give the stereoisomeric esters. However, for use of the novel compounds I for perfumery purposes this separation is normally not necessary.

The esters I exhibit special organoleptic properties, because of which they are outstandingly suitable for use as odorants.

Accordingly, the invention is also concerned with the use of I as odorants and with odorant compositions which are characterised by a content of these esters I.

The compounds I used as odorants in accordance with the invention are in particular distinguished by interesting suggestions of amber. It is of particular interest that these amber notes already occur in the top notes of the odorant compositions. Since on the other hand the compounds I are not excessively volatile, this nuance also remains in the bottom note.

The compounds can accordingly be used, for example, for perfuming such products as cosmetics (soaps, washing agents, detergents, smokers requisites, mouth washes, deodorants, shampoos, lotions, ointments, powders, toilet water, Cologne, extracts etc.), for which purposes the compounds I are preferably not employed alone but in the form of compositions with other odorants.

The compounds I are suitable for use as odorants because of their high capacity for blending harmoniously, especially in combination with a series of natural and synthetic odorants.

The compounds according to the invention harmonise particularly well with the following classes of chemical substances or with the following natural mixtures:

with bergamot oil, hyssop oil, patchouli leaf oil, patchouli oil, vetiver oil, cedarwood oil, cedarleaf oil, galbanum oil, angelica seed oil, petitgrain oil, sandalwood oil, oak moss, labdanum oil, coriander oil, grapefruit oil, Castoreum abs., vetiverol, vetivenyl acetate, natural musk and civet extracts as well as ambergris infusion, with alcohols, such as, e.g., ethanol, propylene glycol, phenylethyl alcohol and phenylpropyl alcohol, geraniol, nerol, citronellol, linalool, santalol, farnesol, terpineol and phenyldimethylcarbinol, with ketones, such as jasmone, dihydrojasmone etc., ionones, irones, Raldeins (methylionones), allylionones, muscone, exaltone, civetone, Versalide (7-acetyl-1,1,4,4-tetramethyl-7-ethyl-1,2,3,4-tetralin), etc., β-mercaptopulegone etc., with aldehydes and their acetals, such as citral, citronellal, hydroxycitronellal, lilial, cyclamenaldehyde, α-hexylcinnamaldehyde, heliotropine, vanillin, phenylacetaldehyde, anisaldehyde etc., with ethers, such as theaspirane, 1-methylcyclododecyl methyl ether, cedryl ether, α- and β-ionyl ether and dihydroionyl ether, guiacyl ether, oestragol, anethole etc., with hydrocarbons, such as limonene, carene, α- and β-pinene, myrcene, ocimene, farnesene etc., with phenolic bodies, such as eugenol, isoeugenol, chavicol etc., with esters, such as linalyl acetate, benzyl acetate, amyl salicylate, cinnamic acid esters, benzyl salicylate, methyl dihydrojasmonate, allyl phenoxyacetate, formyl acetate, styrallyl acetate and phenylethyl phenyl acetate, with lactones, such as α-nonyl-lactone, jasmine-lactone, massoia-lactone, oxahexadecanolide, thibetolide, ethylene brassilate, coumarins, etc., or also with nitrogen-containing bodies, such as pyrazines, e.g. 2,5-dimethylpyrazine, ambrette musk, e.g. ketone musk, etc.

The odorant compositions manufactured using I are in particular also striking because of their exceptional pervasiveness, natural character and vitality.

The concentration of the compounds I can vary within wide limits depending on the end use, for example between about 0.5 (detergents) and about 10% by weight (alcoholic solutions). In perfume bases or concentrates the concentrations can of course also be higher. The perfume bases can be employed in the usual manner for perfuming Colognes, toilet waters, lotions, creams, shampoos, soaps and detergents, etc.

At a low dosage (e.g. 0.5–2%) of I, a distinct increase in pervasiveness is already detectable without an essential change in the basic character of the composition. At higher dosages (e.g. 10–30%) a modification corresponding to the olfactory properties of the compound used occurs additionally.

EXAMPLE 1

(a) A solution of 540 g of 2-cyclohexyl-cyclohexanone in 200 ml of diethyl ether is added dropwise, whilst cooling with ice, to a stirred Grignard solution prepared from 84 g of Mg (filings), 497 g of methyl iodide and 500 ml of diethyl ether. The mixture is left at the reflux temperature overnight and is then cooled, 1 liter of saturated ammonium chloride solution is added, the mixture is subsequently extracted with twice 500 ml of diethyl ether and the organic phase is dried (by means of anhydrous $MgSO_4$) and evaporated in vacuo.

576 g of 1-methyl-2-cyclohexyl-cyclohexanol are obtained and used for the acylation.

(b) A mixture of 360 ml of acetyl chloride and 153 ml of acetic acid anhydride is added dropwise at 0° C., whilst stirring, to a solution of 576 g of crude 1-methyl-2-cyclohexyl-cyclohexanol in 750 ml of N,N-dimethylaniline. The mixture is then allowed to come to room temperature, after which is heated to 40° C. for 36 hours. Thereafter, the reaction mixture is poured onto ice and diluted with 1 liter of ether, and the organic phase is separated off and concentrated on a Rotavapor apparatus. The residue is then taken up in 2 liters of ether and the solution is washed with three times 200 ml of cold 2-N HCl and then with saturated bicarbonate solution and water until neutral, and is dried with anhydrous $MgSO_4$ and evaporated in vacuo. 646 g of crude 1-acetoxy-1-methyl-2-cyclohexyl-cyclohexane are obtained.

Recrystallisation from methanol at −70° C. [or from ethanol at −10° C.] gives 400 g of very pure crystals, melting point 35° C.; odour: diffusive amber note, musk, wood.

Microanalysis: $C_{found}$, 75.57%; $C_{calc.}$, 75.58%; $H_{found}$, 11.16%; $H_{calc.}$, 10.99%.

$IR_{(film)}$: 2960, 2900, 2700, 1735, 1450, 1360, 1270, 1235, 1190, 1150, 1130, 1015, 982, 950, 925, 900, 860, 794, 740 $cm^{-1}$ NMR ($CDCl_3$+TMS): δ=3.1–2.4 ppm (m for 2H); δ=1.98 ppm (s, 3H); δ=1.54 ppm (s, 3H).

MS: m/e: 196 (M+- $CH_2CO$), 178 (M+- AcOH), 163, 149, 136, 121, 109, 97, 81, 71, 67, 55, 43.

EXAMPLE 2

(a) 1 liter of methyl iodide and 1.5 liters of ether are added dropwise in the course of 4½ hours to 384 g of magnesium filings in 2 liters of absolute diethyl ether at the reflux temperature. The mixture is allowed to finish reacting in the course of 12 hours at room temperature; 2.156 kg of 2-(1-methylpropyl)-cyclohexanone in 0.5 liter of ether are then added dropwise, with good cooling. The mixture is kept at the reflux temperature for 12 hours and is cooled and mixed with 1 liter of saturated ammonium chloride solution. It is then poured, in portions, onto a total of 8 kg of ice +0.5 kg of ammonium chloride. After dilution with 3 liters of ether, the mixture is rendered slightly acid with 1 liter of acetic acid, in order to reduce emulsification. The aqueous phase is post-extracted with 1 liter of ether. The combined organic phase is washed with 1 liter of saturated sodium bicarbonate solution and finally with 6 liters of water until neutral. It is then dried with 200 g of anhydrous sodium sulphate and the solvent is evaporated off in vacuo.

The crude product consists of 2.615 kg of 1-methyl-2-sec.-butyl-cyclohexanol containing 5.5% of starting material. The crude product is directly used.

(a') 65 ml (0.13 mol) of methyl-lithium (in ether) are introduced into a 500 ml 3-neck sulphonation flask provided with a thermometer and condenser. 10 g (0.065 mol) of 2-(1-methylpropyl)-cyclohexanone are now slowly added dropwise to this solution at room temperature. After stirring for 5 minutes, water is added to the reaction mixture and the batch is extracted with ethyl ether. The organic phase is then dried over sodium sulphate and concentrated on a rotary evaporator. 10.3 g of the alcohol as described above are obtained.

(b) A mixture of 1.77 kg of acetyl chloride and 0.75 kg of acetic acid anhydride is added dropwise, at 0° C., to a stirred solution of 2.615 kg of the tertiary alcohol, prepared above, in 3.6 kg of N,N-dimethylaniline. The mixture is allowed to come to room temperature and is stirred for 18 hours at 40° C., after which it is slowly poured onto 6 kg of ice and diluted with 3 liters of hexane. The aqueous phase is post-extracted with 1 liter of hexane. The combined organic phase is washed as follows:

Once with 1 liter of 2-N HCl+1 kg of ice
Twice with 2 liters of 2-N HCl
Once with 1 liter of 2-N HCl
Twice with 2 liters of water
Twice with 1 liter of saturated NaHCO$_3$
Once with 1 liter of water; the organic phase is then dried with 0.2 kg of anhydrous Na$_2$SO$_4$ and is evaporated.

The crude product consists of 3.04 kg of 1-acetoxy-1-methyl-2-sec.-butyl-cyclohexane. Content of acetyl compound >85% (gas chromatogram).

Fractionation on a 1 meter packed column (7 mm Raschig rings) gives 2.23 kg of a product with entirely satisfactory olfactory properties: odour: amber, woody, suggesting animal warmth, tobacco-like. B.p.: 39° C./~1×10$^{-3}$ mm Hg;

IR (film): 2950, 2880, 1735, 1462/1450, 1375/1365, 1270, 1240/1230, 1190, 1155, 1020, 945, 860 cm$^{-1}$ NMR (CDCl$_3$+TMS): $\delta$=3.1–2.4 ppm (m, 2H); $\delta$=1.98 ppm (s, 3H); $\delta$=1.53 ppm and 1.50 ppm (s, 3H); $\delta$=0.96 to 0.82 ppm (Doublets and triplets for isomeric secondary and primary methyl groups for 6H).

MS: m/e: 170 (M+- CH$_2$CO), 152 (M+- AcOH), 141, 123, 110, 95, 81/82, 71, 67, 55, 43.

EXAMPLE 3

(a) 20 g of 2 t-butylcyclohexanone are added dropwise, at the reflux temperature, to a Grignard solution prepared from 28 g of methyl iodide and 4.8 g of magnesium. The reaction mixture is then allowed to reflux for 24 hours. Thereafter it is poured onto ice/ether and extracted. The organic phase is dried over sodium sulphate and concentrated. The crude product contains 68% of 1-methyl-1-hydroxy-2-t-butyl-cyclohexane (in addition to 32% of starting ketone), b.p. 97°/11 mm Hg.

IR (liq.): 3500 cm$^{-1}$
NMR (CDCl$_3$): 1 ppm (9H) s; 1.4 ppm (3H) s
MS: m/e: 170, 155, 137, 110, 96, 81, 71, 57, 43.

(b) A mixture of 16 ml of acetyl chloride and 8 ml of acetic acid anhydride is added dropwise, at 0° C., to a solution of 20 g of the alcohol in 41.6 ml of N,N-dimethylaniline. The reaction mixture is allowed to come to room temperature and is stirred for 24 hours. It is then poured onto ice and extracted with ether. The organic layer is subsequently washed with 2 N hydrochloric acid and saturated sodium bicarbonate and is dried over sodium sulphate. The organic phase is concentrated. The crude mixture contains (according to a gas chromatogram) 32% of 2-t-butyl-cyclohexanone, 20.4% of 1-methyl-1-hydroxy-2-t-butyl-cyclohexane and 47.5% of 1-acetoxy-1-methyl-2-t-butylcyclohexane. Distillation at 0.2 mm Hg gives, in addition to less pure fractions, 2 g of 98% pure 1-acetoxy-1-methyl-2-t-butyl-cyclohexane; boiling point 48°–53° C./0.2 mm Hg.

IR (liq.): 1730 cm$^{-1}$, 1360, 1260, 1230, 1150, 1180, 1015 cm$^{-1}$

NMR (CDCl$_3$): 1 ppm (9H) s; 1.7 ppm (3H) s; 2 ppm (3H) s.

MS: m/e: 212, 170, 137, 110, 96, 81, 71, 57, 43.

Odour: ambra-like, woody, cedar-like, patchouli, vetiver.

In the formulation examples which follow, the unexpected organoleptic properties of the novel sec. butyl derivative are compared, by means of typical scent compositions, with the structurally closely related 1-acetoxy-1-ethyl-2-sec.butylcyclohexane, hereinafter referred to as "ethyl derivative", and with 1-acetoxy-1-vinyl-2-sec. butyl-cyclohexane ("vinyl derivative") (U.S. Pat. Nos. 3,769,330 and 3,852,219).

EXAMPLE 4

Perfumery base with sage-like character

|   | Parts by weight |
|---|---|
| Methyl-dihydrojasmonate | 400 |
| Bergamot oil | 200 |
| Hyssop oil | 100 |
| Patchouli leaf oil | 100 |
| Allylionone | 60 |
| Propylene glycol | 120 |
|   | 980 |

By adding 2% of 1-acetoxy-1-methyl-2-sec.-butyl-cyclohexane, a typical warm sage effect is achieved in this spicy-green composition, which effect is exceptionally suitable for men's toiletries.

In contrast thereto, the addition of the same amount of ethyl derivative does not produce this desired sage effect; in this case, the composition has a dry-woody and honey-like impact, i.e. the only result is to emphasise the hyssop oil note.

EXAMPLE 5

Perfumery composition, in the direction of tomato

|   | Parts by weight |
|---|---|
| Bergamot oil | 300 |
| Corps Cassis Givaudan (8-mercaptomenthone) | 320 |
| Grapefruit oil | 160 |
| Galbanum oil | 120 |
| Gamma-nonyl-lactone (10% strength in alcohol) | 60 |
| 2,5-Dimethyl-pyrazine | 10 |
|   | 970 |

The addition of 3% of 1-acetoxy-1-methyl-2-sec.butyl-cyclohexane to the above composition produces, in the fruity-green base, a surprising tomato leaf note which on the other hand cannot be achieved with the ethyl derivative. The latter compound merely emphasises the original fruity-citruslike character of the base.

EXAMPLE 6

Perfumery base with green character

|  | Parts by weight |
| --- | --- |
| Isoraldein | 200 |
| Petitgrain oil | 100 |
| Galbanum oil | 100 |
| Musc 174 ® Givaudan (Oxa-4-pentadecanolide) | 100 |
| Bergamot oil | 60 |
| Angelica seed oil | 40 |
| Propylene glycol | 380 |
|  | 980 |

The addition of 2% of 1-acetoxy-1-methyl-2-sec.butyl-cyclohexane to the above green base achieves a pronounced amber character which cannot be achieved by the same dose of ethyl derivative. On the other hand, a higher dose of the ethyl derivative cannot be used in the composition, since the character of the latter would otherwise change.

EXAMPLE 7

Cologne base

|  | Parts by weight |
| --- | --- |
| Linalyl acetate | 200 |
| Phenylethyl alcohol | 150 |
| Benzyl salicylate | 100 |
| Geraniol | 100 |
| Methyl 1-methylcyclododecyl ether | 100 |
| Linalool | 50 |
| Ethylene brassylate | 50 |
| Methyl dihydrojasmonate | 30 |
| Hydroxycitronellal | 50 |
| α-Ionone | 30 |
| Lilial Givaudan (4-tert. butyl-phenyl-2-methyl-propanal) | 20 |
| Vetiverol | 20 |
| Santalol | 20 |
| Allyl phenoxyacetate | 10 |
| Bornyl acetate | 10 |
| Styrallyl acetate | 10 |
|  | 950 |

If 5% of 1-acetoxy-1-methyl-2-sec.butyl-cyclohexane is added to the above Cologne base, the latter has a much more harmonious, pleasantly rosy and fresher impact.

The addition of the same amount of ethyl derivative results in a suppression of the Cologne note.

EXAMPLE 8

Chypre composition

|  | Parts by weight |
| --- | --- |
| Madrox ® (methyl 1-methyl-cyclododecyl ether) | 120 |
| Phenylethyl phenylacetate | 100 |
| Bergamot oil | 100 |
| α-Ionone | 100 |
| a-Hexylcinnamaldehyde | 100 |
| Benzyl acetate | 50 |
| Vetivenyl acetate | 80 |
| Citronellol | 70 |
| Linalool | 70 |

-continued

|  | Parts by weight |
| --- | --- |
| Patchouli oil | 30 |
| Sandalwood oil | 30 |
| Absolute oak moss, decolorised | 30 |
| Eugenol | 30 |
| Ketone musk | 30 |
| Ambrette musk | 20 |
| French labdanum oil | 5 |
| Coriander oil | 5 |
|  | 970 |

If 3% of 1-acetoxy-1-methyl-2-sec.butyl-cyclohexane is added to the above chypre composition, the latter acquires a pronounced warm ambra character which imparts substantially more diffusion and at the same time tenacity to the composition.

If the ethyl derivative is used as a component, it merely causes the same composition to be more powdery.

EXAMPLE 9

Carnation base

|  | Parts by weight |
| --- | --- |
| Eugenol | 300 |
| Isoeugenol | 175 |
| Benzyl salicylate | 100 |
| Amyl salicylate | 50 |
| Phenylethyl phenyl acetate | 50 |
| Citronellol | 50 |
| α-Ionone | 50 |
| Hydroxycitronellal | 50 |
| α-Hexylcinnamaldehyde | 50 |
| Benzyl acetate | 50 |
| Terpineol | 30 |
| Heliotropine | 20 |
|  | 975 |

The addition of 0.5–1% of 1-acetoxy-1-methyl-2-sec.-butyl-cyclohexane already suffices to achieve the same effect as with 5 times this amount of ethyl derivative.

EXAMPLE 10

Perfumery (moss) base

|  | Parts by weight |
| --- | --- |
| Hydroxycitronellal | 200 |
| Bornyl acetate | 300 |
| Terpenyl acetate | 180 |
| α-Hexylcinnamaldehyde | 100 |
| Benzyl acetate | 50 |
| Linalool | 40 |
| α-Ionone | 20 |
| Styrallyl acetate | 20 |
| Cypress oil | 20 |
| Rosemary oil | 10 |
| C-12-Aldehyde (laurinaldehyde) (10% strength in propylene glycol) | 10 |
| Lavandine oil | 10 |
| Eugenol | 10 |
| Citral | 6 |
| p-Menthane-8-thiol-3-one | 4 |
|  | 980 |

If 20 parts of 1-acetoxy-1-methyl-2-sec.butyl-cyclohexane are added to this fresh forest base, the resulting base has a much warmer and woodier effect and possesses more volume. A new note, in the direction of chypres, manifests itself.

In contrast, the addition of 20 parts of the vinyl derivative produces no change in the original base.

EXAMPLE 11

Perfumery base (Fougère)

|  | Parts by weight |
|---|---|
| Lavender oil | 200 |
| Amyl salicylate | 200 |
| Coumarin | 100 |
| Tree moss (50% in propylene glycol) | 100 |
| Citronellol | 60 |
| Geraniol | 60 |
| Ambrette musk | 60 |
| Bergamot oil | 60 |
| α-Ionone | 20 |
| Vetiver oil | 20 |
| Sandalwood oil | 20 |
| α-Amylcinnamaldehyde | 20 |
| Eugenol | 20 |
| Patchouli oil | 20 |
|  | 960 |

The addition of 40 parts of 1-acetoxy-1-methyl-2-sec.-butyl-cyclohexane provides the composition with much more pervasiveness and volume. The base has a much warmer, woodier and more rounded impact.

On the other hand, the addition of 40 parts of vinyl derivative results in no improvement of the composition.

EXAMPLE 12

Perfumery base (men's Cologne direction)

|  | Parts by weight |
|---|---|
| Synthetic bergamot | 120 |
| Cedryl acetate | 100 |
| Synthetic lemon oil | 80 |
| α-Ionone | 80 |
| Olibanum oil | 60 |
| Sandela ® Givaudan (3-isocamphyl-5-cyclohexanol) | 60 |
| Madrox^R | 60 |
| Fixolide ® Givaudan (1,1,2,4,4,7-hexamethyl-6-acetyl-1,2,3,4-tetrahydronaphthalene) | 60 |
| Linalool | 60 |
| Hydroxycitronellal | 50 |
| Benzyl acetate | 40 |
| cis-Jasmone | 10 |
| Galbanum oil | 10 |
| Styrallyl acetate | 10 |
| Coumarin | 10 |
| Heliotropine | 10 |
| C-10-Aldehyde (10% strength in propylene glycol) | 10 |
| C-11-Aldehyde (10% strength in propylene glycol) | 10 |
| Artemisia oil | 10 |
| Cyclal C ® Givaudan (3,5-dimethyl-cyclohex-3-en-1-ylcarboxaldehyde) | 10 |
| Synthetic castoreum oil | 10 |
| Agrumex ® Givaudan (o-tert.-butyl-cyclohexyl acetate) | 10 |
| White thyme oil | 10 |
| French Ciste labdanum oil | 10 |
| Rectified clove oil | 10 |
| Estragol | 6 |
| Fructone ® IFF (2-methyl-1,3-dioxolan-2-ethyl acetate) | 6 |
| Isobutylquinoleine (10% strength in propylene glycol) | 8 |
| Geranyl acetate | 20 |
|  | 950 |

If 50 parts of 1-acetoxy-1-methyl-2-sec.butyl-cyclohexane are added to the above base, which per se is already suitable for men's toiletries, the novel composition has a warmer, more rounded and fuller impact. A very desirable note, suggesting animal warmth, now manifests itself.

The addition of 5 parts of the vinyl derivative has no effect on the base.

EXAMPLE 13

A. Tenacity on textiles (substantivity)

The substantivity of 1-acetoxy-1-methyl-2-sec.butyl-cyclohexane (a), of the ethyl derivative (b) and of the vinyl derivative (c) was examined by washing experiments under various conditions.

| Wash temperature | |
|---|---|
| 10° | hand-washed laundry |
| 60° | machine laundry |
| 95° | machine laundry |

A panel of 10 persons concluded that under all conditions (a) showed up by far the best, namely: (a) proved stronger and more tenacious on the washed laundry, and the textiles treated in this way left the typical impression of clean laundry.

A comparison of the substantivity gave the following picture:

| Compound | Comparative rating for substantivity |
|---|---|
| (a) | 2 |
| (b) | 0.5 |
| (c) | 0.7 |

B. Dilution series

Dilution series of 100%, 10%, 1%, 0.1% and 0.01% were prepared with products (a), (b) and (c). Once again it was immediately obvious that the product (a) exhibited by far the lowest odour threshold value on the scent test strip: at 0.1 and 0.01%, only (a) remained perceptible.

C. Incorporation into bases

Incorporation into bases of the Fougere, moss and Ligne masculine type showed that concentrations of 2, 3 and 4% by weight of (a) sufficed entirely to upgrade these bases, whilst such was not the case with (b) and (c). In the latter cases, 5–10% was necessary to achieve the same effect.

What is claimed is:

1. A fragrance composition containing an olfactorily effective amount of a compound of the formula

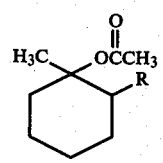

wherein R represents sec. butyl, tert. butyl or cyclohexyl and at least one other olfactory agent.

2. A fragrance composition of claim 1 containing an olfactorily effective amount of 1-acetoxy-1-methyl-2-sec. butyl-cyclohexane.

3. A fragrance composition of claim 1 containing an olfactorily effective amount of 1-acetoxy-1-methyl-2-tert. butyl-cyclohexane.

4. A fragrance composition of claim 1 containing an olfactorily effective amount of 1-acetoxy-1-methyl-2-cyclohexyl-cyclohexane.

* * * * *